Jan. 7, 1975 C. H. TASCHE Plant Pat. 3674
CALLISTEMON PLANT
Filed Aug. 20, 1973
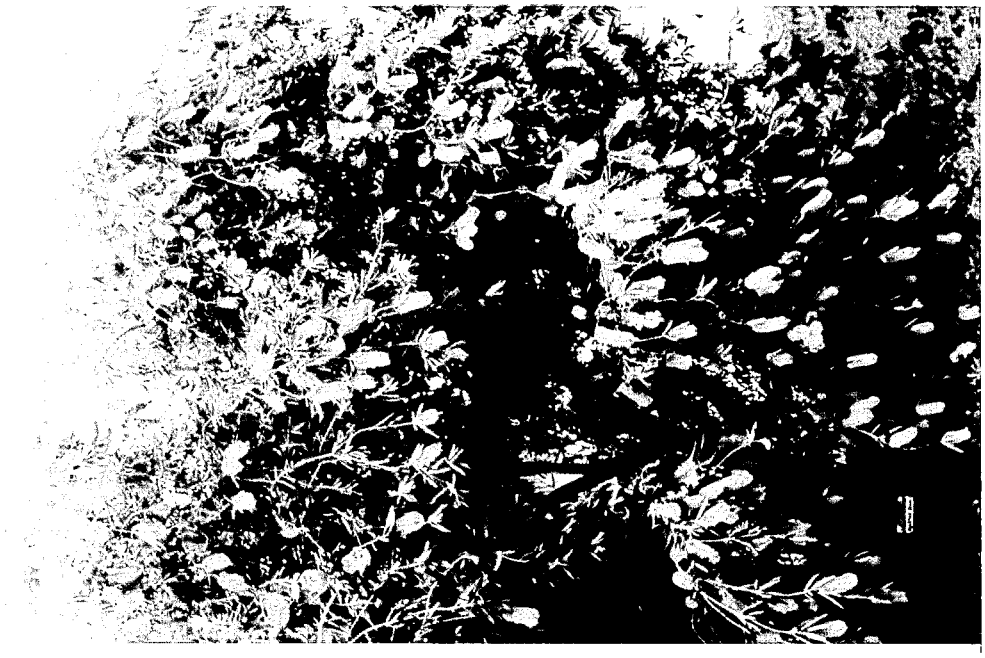
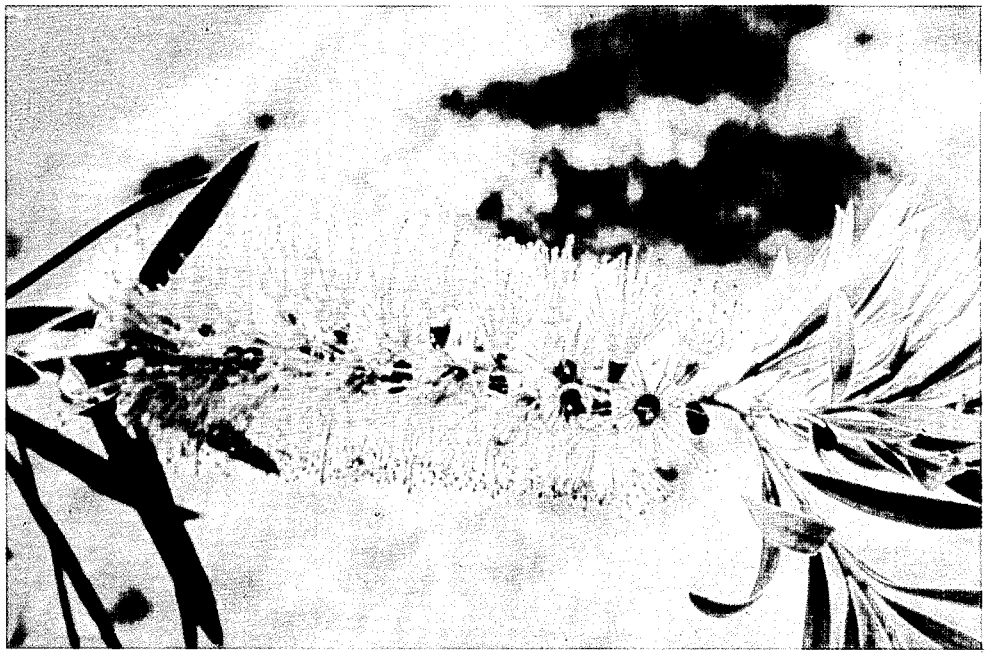

United States Patent Office

Plant Pat. 3,674

Patented Jan. 7, 1975

3,674
CALLISTEMON PLANT

Carl H. Tasche, 5470 El Jardin St.,
Long Beach, Calif. 90815

Filed Aug. 20, 1973, Ser. No. 389,574
Int. Cl. A01h 5/00
U.S. Cl. Plt.—54 1 Claim The present invention relates to a new and distinct variety of Callistemon plant which was discovered by me in Australia and which was grown and tested by me in my experimental gardens located at Long Beach, Calif. as a selected cultivated hybrid seedling of unknown parentage.

Prior to my discovery of this new seedling, I had been interested for a long time in experimenting with and developing many plants native to Australia and Africa, and I found in Australia a Callistemon variety which I recognized as being unusually attractive and distinctive. In due course, I acquired several cuttings of this particular new variety which I planted in my experimental gardens located in California, and I continued to observe and test the same preparatory to commercially introducing the new variety in the United States.

During my experimental work with these seedlings, my attention was attracted to one particular seedling which had an unusually attractive, soft and graceful weeping habit, with pendant lateral branches, especially when in bloom, originating in spaced horizontal whorls from upright single or branched leaders, forming an upright and compact large shrub which becomes a small tree in time. In addition, this plant bore exceptionally large and attractive brilliant red bottlebrush flower spikes ranging from 6 to 10 inches in length and of larger diameter than those of common Callistemon species and prolifically produced in clusters of 6 to 10 or more, originating from a single point. Still another distinutive feature of this plant which attracted my attention was that multiple terminal growth shoots, usually from 5 to 10 shoots, grew from the ends of most flowering spikes, instead of the usual single or few new growths, thereby producing an unusually high foliage density and clustering of subsequent flowering branches. The color of the new foliage was observed as an attractive light greenish-bronze color.

The over-all effect of mature plants of my new seedling at the time of flowering was a densely foliated small tree ranging from 10 to 15 or more feet tall, entirely clothed in softly pendant, brilliantly colored branches. After bloom and making new growth, the plants attain a more stiff habit similar to other upright Callistemon types, but are more graceful. With appropriate pruning, I have found that my new seedling is very suitable and striking as a street tree, and equally good as a flowering shrub or tree for lawn and garden decorative plantings.

Prolonged observation of my new seedling and progeny thereof asexually reproduced therefrom by softwood cuttings, as planted by me in my gardens aforementioned, have convinced me that my new seedling is definitely a new and distinct Callistemon variety and that its characteristics and distinctions referred to in the foregoing come true to form and are established and transmitted through succeeding propagations.

The accompanying drawing shows a typical mature plant of my new Callistemon variety as it appears when in bloom, as well as a close-up view of a typical flower spike, all as depicted in color as nearly true as it is reasonably possible to make the same in a color illustration of this character.

The following is a detailed description of my new Callistemon variety, with color terminology in accordance with Maerz & Paul Dictionary of Color, except where Ridgway's Color Standards and Nomenclature is indicated or where general color terms of ordinary dictionary significance are obvious, as based on observations made at my nurseries at Long Beach, Calif.

PLANT

Type: Large shrub, becoming a small tree in time.

Class: Somewhat intermediate between *Callistemon viminalis* and more rigid upright species.

Breeding: Hybrid seedling of unknown parentage.

Propagation: Holds its distinguishing characteristics through succeeding propagations by softwood rooted cuttings.

Form: An upright, openly compact, large shrub or small tree, with gracefully pendant lateral branches, especially when in flower, originating in spaced horizontal whorls from upright single or branched leaders; attains height of 10 to 15 or more feet when mature.

Growth habit: Vigorous; flowers at an early age on clusters of new growth emanating from one point.

Blooming habit: Primarily May–June in Southern California, and occurring again from fall growth and flowering flushes as is common with other Callistemon species in Southern California.

Foliage:

*Leaves.*—Lanceolate; smooth; entire; stiffly rigid; borne scattered and uprightly angularly to the stem on short petioles. Length—From about 3 inches to 4 inches long at maturity. Width—From about ⅜ inch to ½ inch wide at maturity. Color—Mature leaves—Under side—From near Cossack Green, Plate 23, H 11 to near Cossack Green, Plate 23, J 11. Upper side—Slightly lighter in range of Meadowgrass Green, Plate 23, H 9. Young leaves—Progressively lighter green with immaturity, with new growth being tinged with reddish bronze color.

FLOWERS

Flowering habit: Flowers produced prolifically in terminal spikes ranging from 6 inches to 10 inches in length and over 2½ inches in diameter, and tending to form clusters from a single branching point; from about 40 to 50 or more florets per spike; stamens and anthers dark red in color; stamens about ½ inch or more long; filaments united at base into 5 bundles and bundles are united into a short tube or ring; all stamens fall off as a single unit.

Buds:

*Color.*—Grayish.

Flowers:

*Color.*—Bright red, in ranges from near Geranium, Plate 2, 10 K to Spark, Plate 2, 10 L to Cheery Phantom Red, Plate 2, 12 L or sometimes from near Rose Red, Plate 12, 71 b to Spectrum Red, Plate 1,3 (Ridgway).

FRUIT

Fruit: Sterile abortive seed capsules, shedding soon after flowering.

GENERAL OBSERVATIONS

Hardiness: Extremely hardy; young plants have withstood minimum temperatures as low as 20° F. without injury in Southern California.

Disease resistance: None encountered in Southern California, as determined by observations and comparisons with other Callistemon varieties grown in this region Culture: My new variety has been grown successfully in heavy soil overlying limestone, in sandy loam overlying decomposed granite in San Diego County, Calif., and in porous growing mixtures in containers at Carson, Calif.; early growth from rooted cuttings has been vigorous, with good flowering the first year after propagation; plants respond well to ample watering by drip irrigation, as well as by other usual methods, and by hand-watering when grown in containers.

I claim:

1. A new and distinct variety of Callistemon plant, substantially as herein shown and described, characterized particularly as to novelty by the unique combination of an attractive and graceful, soft weeping habit of growth, with pendent lateral branches, especially when in bloom, originating in spaced horizontal whorls from upright single or branched leaders, forming an upright and compact large shrub which becomes a small tree in time, dense and attractive green foliage which is light greenish-bronze when young and forming multiple new terminal growth shoots emanating from the ends of most flowering spikes and contributing to an unusual foliage density and clustering of subsequent flowering branches, large brilliant red bottlebrush flower spikes, ranging up to ten inches in length and of larger diameter than those of common species, said spikes being prolifically produced in clusters of six to ten or more emanating from one point, and a habit of producing sterile abortive seed capsules which shed immediately after flowering instead of persisting on the branches as is typical of most species.

References Cited

Flowering Trees of the World, Menninger, 1962, p. 170 and plate 247 relied on.

ROBERT E. BAGWILL, Primary Examiner